United States Patent [19]

Mixan et al.

[11] 4,048,213

[45] Sept. 13, 1977

[54] (((ARYL)THIO)METHYLENE)-PROPANEDINITRILES

[75] Inventors: Craig E. Mixan; R. Garth Pews, both of Midland, Mich.

[73] Assignee: The Dow Chemical Company, Midland, Mich.

[21] Appl. No.: 742,037

[22] Filed: Nov. 15, 1976

[51] Int. Cl.$^2$ ............................................. C07C 121/70
[52] U.S. Cl. ................................... 260/465 F; 71/98; 260/465 G; 260/465 H; 424/304
[58] Field of Search ............ 260/465 H, 465 G, 465 F

[56] References Cited

U.S. PATENT DOCUMENTS

| 3,050,545 | 8/1962 | Heininger et al. | 260/465 |
|---|---|---|---|
| 3,590,068 | 6/1971 | Toepfl et al. | 260/465 |
| 3,828,091 | 8/1974 | Strong | 260/465 F |

OTHER PUBLICATIONS

Westfahl, Chemical Abstracts, vol. 52, 14659–14660.

Primary Examiner—Dolph H. Torrence
Attorney, Agent, or Firm—Daniel L. DeJoseph; C. Kenneth Bjork

[57] ABSTRACT

Disclosed are novel (((aryl)thio)methylene)-propanedinitriles which have utility as antimicrobials, herbicides, insecticides, and fungicides.

12 Claims, No Drawings

(((ARYL)THIO)METHYLENE)-PROPANEDINITRILES

SUMMARY OF THE INVENTION

The novel compounds of this invention are (((aryl)thio)methylene)-propanedinitrile compounds of the formula

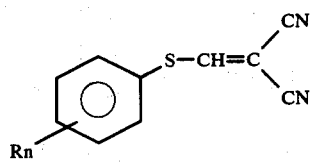

and also of the formula

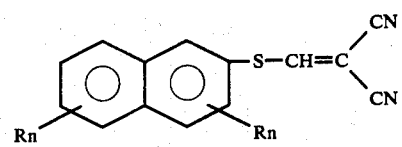

wherein, in both formulas, each R substituent individually represents F, Cl, Br, a straight or branched chain alkyl group, or an alkoxy group, said groups having from 1 to 4 carbon atoms, and n is an integer with a value of 0, 1 or 2.

These compounds have utility as antimicrobials, herbicides, insecticides and fungicides.

The novel compounds of the present invention are prepared by allowing substantially one molar equivalent of ethoxymethylene malononitrile to react with substantially one molar equivalent of the appropriate arylthiol at from about 25° C to about 75° C for from about ¼ hour to about 1 hour in the presence of an alcoholic solvent such as alcohol. The desired product can be collected by crystallization from the reaction mixture, by elution from a chromatographic column or by other conventional separatory techniques.

DESCRIPTION OF SOME PREFERRED EMBODIMENTS

The following examples illustrate the present invention and the manner by which it can be practiced but as such should not be construed as limitations upon the overall scope of the same. The product compounds are identified by elemental analysis and nuclear magnetic resonance spectroscopy.

EXAMPLE 1

Preparation of (((4-methylphenyl)thio)-methylene)-propanedinitrile

To a solution of 12.2 g (0.1 mole) of ethoxymethylene malononitrile in 75 ml of ethanol, was added 12.4 g (0.1 mole) of p-thiocreosol in 75 ml of ethanol. The reaction mixture was heated to approximately 60° C and stirred for one hour, and then partially reduced in volume. The solution was cooled and the desired product crystallized in crude form. The crude product was purified by recrystallization from ethanol to give 6.25 g of tan crystals, melting point 110°–111.5° C, which were identified as (((4-methylphenyl)thio)methylene)-propanedinitrile, corresponding to the formula

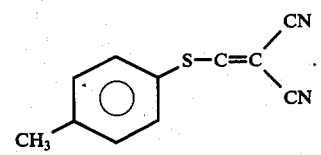

Anal. Theory: C, 66.00; H, 4.00; N, 14.00; S, 16.00. Found: C, 66.3; H, 4.04; N, 13.95; S, 16.0.

The yield of the desired product was calculated to be 31%, based on the p-thiocreosol.

Using a similar method and employing the appropriately substituted starting materials, the compounds of Examples 2–10 were prepared. These compounds and their melting points, elemental analyses and physical appearances are set forth in Table 1.

TABLE 1

| Example | Compound | Appearance | Melting Point (° C) | Found C | Found H | Found N | Found S | Theory C | Theory H | Theory N | Theory S |
|---|---|---|---|---|---|---|---|---|---|---|---|
| 2 | (((4-Bromophenyl)thio)methylene)-propanedinitrile | tan crystals | 140–142.5 | 45.3 | 2.10 | 10.67 | 12.1 | 45.28 | 1.89 | 10.57 | 12.08 |
| 3 | (((3-Chlorophenyl)thio)methylene)-propanedinitrile | beige crystals | 97–98 | 54.4 | 2.44 | 12.77 | 14.5 | 54.42 | 2.27 | 12.70 | 14.51 |
| 4 | (((4-Fluorophenyl)thio)methylene)-propanedinitrile | beige crystals | 90–91.5 | 58.7 | 2.58 | 13.88 | 15.8 | 58.82 | 2.45 | 13.73 | 15.69 |
| 5 | (((4-Methoxyphenyl)thio)methylene)-propanedinitrile | light brown crystals | 111–113 | 61.1 | 3.81 | 12.71 | 14.9 | 61.11 | 3.70 | 12.96 | 14.81 |
| 6 | ((2-Naphthalenylthio)methylene)-propanedinitrile | brownish-yellow solid | 152.5–154 | 71.0 | 3.64 | 11.80 | 13.5 | 71.19 | 3.39 | 11.86 | 13.56 |
| 7 | (((2,5-Dichlorophenyl)thio)-methylene)-propanedinitrile | pale yellow | 108.5–110 | 46.9 | 1.83 | 10.92 | 12.3 | 47.06 | 1.57 | 10.98 | 12.55 |
| 8 | (((3,4-Dichlorophenyl)thio)methylene)-propanedinitrile | pale yellow solid | 109–111 | 47.2 | 1.84 | 10.64 | 12.8 | 47.06 | 1.57 | 10.98 | 12.55 |
| 9 | (((4-Bromo-3- | light brown | 129–131 | 47.0 | 2.77 | 10.03 | 11.3 | 47.31 | 2.51 | 10.04 | 11.47 |

TABLE 1-continued

| Example | Compound | Appearance | Melting Point (° C) | Found C | H | N | S | Theory C | H | N | S |
|---|---|---|---|---|---|---|---|---|---|---|---|
| | methylphenyl)-thio)methylene)-propanedinitrile | crystals | | | | | | | | | |
| 10 | (((4-(1,1-Dimethylethyl)phenyl)thio)methylene)-propanedinitrile | pale yellow solid | 73–75 | 69.5 | 5.93 | 11.59 | 13.3 | 69.42 | 5.79 | 11.57 | 13.22 |

The compounds of Examples 2, 3, 4, 5, 6, 9 and 10 were recovered by recrystallization from ethanol; the compounds of Examples 7 and 8 were recovered by elution with $CHCl_3$ from a silica gel column.

These compounds will heretofor be referred to by number only. For example, the compound of Example 5 [(((4-methoxyphenyl)thio)methylene)-propanedinitrile], will be referred to as Compound 5.

The (((aryl)thio)methylene)-propanedinitrile compounds of the invention are useful as antimicrobial agents for the control of bacteria and fungi. This is not to suggest that these compounds and mixtures thereof with usual additives are equally effective against all such organisms at the same concentration. For such uses, these compounds can be employed in an unmodified form or in the form of a liquid or finely-divided solid composition. Thus, the compounds can be dispersed in a finely-divided solid and employed as a dust. Such mixtures can also be dispersed in water with the aid of a surface-active agent and the resulting emulsion employed as a spray. In other procedures, the (((aryl)-thio)-methylene)-propanedinitrile compounds can be employed as the active constituents in solvent solutions, oil-in-water or water-in-oil emulsions. The augmented compositions are adapted to be formulated as concentrates and subsequently diluted with additional liquid or solid adjuvants to produce the ultimate treating compositions. Good results are obtained when employing compositions containing antimicrobial concentrations and usually from about 100 to about 1000 parts by weight of one or more of the compounds per million parts of such compositions.

Compounds of the present invention have also displayed utility as herbicides, insecticides and fungicides.

The compounds can be employed as pesticides by distributing the compound, in a pesticidally-effective quantity and usually in the form of a composition containing adjuvants to aid in dispersing the same, so as to contact directly the plant or other organism to be controlled or, alternatively, so as to contact the growth medium or habitat of the organisms whereby eventual contact with said organisms will be established. For the control of weeds and other higher plant pests, the organisms are contacted with a pesticidal amount which is also a herbicidal amount of the compound. Thus, many weed pests are controlled by the distribution in soil of from about 1 to 50 pounds or more of the chemical per acre so as to contact seeds and emerging seedlings of the vegetation to be controlled. For the control of bacterial and fungal pests, including these forms occurring in various paint, paper pulp and wood impregnating formulations, the active chemicals are applied in the form of compositions containing from 100 to 1000 or more parts of the chemical per million parts by weight of the composition.

In representative antimicrobial activity tests, selected (((aryl)thio)methylene)-propanedinitrile compounds of the present invention were separately dispersed in warm melted nutrient agar which was then poured into petri dishes and allowed to solidify, the (((aryl)thio)methylene)-propanedinitrile compounds being employed in an amount sufficient to provide from 10 to 500 parts by weight thereof per million parts (ppm) of the ultimate agar composition. The surface of the agar was then inoculated with a variety of bacterial and fungal pest organisms, and the inoculated plates were incubated under conditions conducive to bacterial and fungal growth. Similar check plates in which the agar contains no active (((aryl)thio)methylene)-propanedinitrile or other toxic compounds were similarly inoculated and incubated.

In such an operation, Compound 1 [(((4-methylphenyl)thio)methylene)-propanedinitrile] gave 100% growth inhibition (kills) and control of the organism Myco. phlei at a concentration of 500 ppm.

In similar antimicrobial activity tests, the compounds which are listed in Table 2 by number gave 100% kill and control of the following organisms at the indicated concentration in ppm.

TABLE 2

Antimicrobial Activity

| Organism | Compound Number (Conc. in ppm) | | | | | |
|---|---|---|---|---|---|---|
| | 2 | 3 | 4 | 5 | 6 | 8 |
| Myco. phlei | 500 | 10 | 100 | 500 | 500 | 500 |
| T. mentagrophytes | — | 500 | 100 | — | 500 | — |
| B. subtilis | — | 500 | 100 | — | — | — |
| C. pelliculosa | — | — | 100 | — | — | — |
| P. pullulans | — | — | 100 | — | — | — |
| C. ips | — | — | 500 | — | — | — |
| T. Sp. Madison P-42 | — | — | 100 | — | 500 | — |

In similar tests, the Compound 7 [(((2,5-dichlorophenyl)thio)methylene)-propanedinitrile], gave 50% control of the organisms B. subtilis and Myco. phlei at a concentration of 500 ppm.

In representative pre-emergence herbicidal activity tests, selected (((aryl)thio)methylene)-propanedinitrile compounds of the present invention were separately formulated in an aqueous-emulsified composition which contained about 100 parts by weight of the active test compound per million parts of the aqueous composition. The selected (((aryl)thio)methylene)-propanedinitrile compounds were applied in such a form as a soil drench at a dosage rate of 10 lbs of active chemical per acre. Table 3 lists the percent control these compounds gave of various plant species.

TABLE 3
Pre-Emergent Herbicidal Activity
(Percent Control at 10 lbs/acre level)

| Plant | \multicolumn{5}{c}{Compound Number} | | | | |
|---|---|---|---|---|---|
|  | 1 | 2 | 3 | 4 | 5 |
| Pigweeds | 100 | — | — | — | — |
| Crabgrass | 90 | — | 50 | 50 | — |
| Barnyard Grass | — | — | — | 80 | — |
| Wild Oats | — | — | — | 10 | — |
| Yellow Foxtail | 20 | — | — | 10 | 10 |
| Nutsedge | — | 70 | — | — | — |
| Morning Glory | 80 | — | — | — | — |

In representative post-emergency herbicidal tests, selected (((aryl)thio)methylene)-propanedinitrile compounds of the present invention were separately formulated in an aqueous dispersion so that there were about 4,000 parts by weight of the active test compounds per million parts of the aqueous composition. The plants listed in Table 4 were then sprayed to run-off with the aqueous formulation, and the Table lists the percent control each of the selected (((aryl)thio)methylene)-propanedinitrile compounds gave of each plant.

TABLE 4
Post-Emergent Herbicidal Activity
(Percent Control at 4,000 ppm)

| Plant | \multicolumn{7}{c}{Compound Number} | | | | | | |
|---|---|---|---|---|---|---|---|
|  | 1 | 2 | 3 | 4 | 5 | 8 | 10 |
| Pigweeds | 100 | 100 | 100 | 100 | 100 | — | 35 |
| Cotton | — | — | — | 50 | 20 | — | 40 |
| Crabgrass | 30 | — | 50 | 50 | 100 | — | 35 |
| Barnyard Grass | 20 | — | 20 | 20 | 20 | — | — |
| Wild Oats | 20 | 10 | 20 | 20 | 20 | — | 25 |
| Yellow Foxtail | — | — | 20 | 20 | 80 | — | 15 |
| Velvetleaf | — | — | — | 90 | 50 | 50 | 35 |
| Nutsedge | — | — | 90 | — | — | — | — |
| Morning Glory | — | — | — | 40 | 40 | 35 | 75 |

In representative insecticidal operations, Compound 1 exhibited 80% control of the cabbage looper at a concentration of 400 ppm and 50% control of the two-spotted spider mie at 400 ppm; Compound 2 exhibited 100% control of both the cabbage looper and the western-spotted cucumber beetle larvae at concentrations of, respectively, 400 ppm and 24 ppm; Compound 3 exhibited 40% control of the cabbage looper at 400 ppm and 100% of both the western-spotted cucumber beetle larvae and the two-spotted spider mite at concentrations of, respectively, 25 ppm and 400 ppm; Compound 5 exhibited 60% control of the cabbage looper at 400 ppm and 100% control of the two-spotted spider mite at 400 ppm; and Compound 4 exhibited 60% control of the cabbage looper at 100 ppm.

In representative plant fungicidal operations Compound 1 exhibited 95% control of apple scab fungus at 100 ppm; both Compound 5 and Compound 6 exhibited 100% control of tobacco black shank at 25 ppm, and Compound 6 also exhibited 75% control of apple scab fungus at 100 ppm; Compound 8 exhibited 50% control of downey mildew at 100 ppm; Compound 9 exhibited 75% control of bean mildew at 100 ppm; and Compound 10 exhibited 90% control of apple scab fungus at 100 ppm.

What is claimed is:

1. A compound of the formula $$\text{R}_n\text{-C}_6\text{H}_4\text{-S-CH=C(CN)}_2$$

wherein
   each R substituent individually represents F, Cl, Br, a straight or branched chain alkyl group, or an alkoxy group, said groups having from 1 to 4 carbon atoms, and $n$ is an integer with a value of 0, 1 or 2.

2. The compound of claim 1 which is (((4-bromophenyl)thio)methylene)-propanedinitrile.

3. The compound of claim 1 which is (((3-chlorophenyl)thio)methylene)-propanedinitrile.

4. The compound of claim 1 which is (((4-fluorophenyl)thio)methylene)-propanedinitrile.

5. The compound of claim 1 which is (((4-methoxyphenyl)thio)methylene)-propanedinitrile.

6. The compound of claim 1 which is (((4-methylphenyl)thio)methylene)-propanedinitrile.

7. The compound of claim 1 which is (((2,5-dichlorophenyl)thio)methylene)-propanedinitrile.

8. The compound of claim 1 which is (((3,4-dichlorophenyl)thio)methylene)-propanedinitrile.

9. The compound of claim 1 which is (((4-bromo-3-methylphenyl)thio)methylene)-propanedinitrile.

10. The compound of claim 1 which is (((4-(1,1-dimethylethyl)phenyl)thio)methylene)-propanedinitrile.

11. A compound of the formula $$\text{R}_n\text{-C}_{10}\text{H}_6\text{-S-CH=C(CN)}_2$$

wherein
   each R substituent individually represents F, Cl, Br, a straight or branched chain alkyl group, or an alkoxy group, said groups having from 1 to 4 carbon atoms, and $n$ is an integer with a value of 0, 1 or 2.

12. The compound of claim 11 which is ((2-naphthalenylthio)methylene)-propanedinitrile.

* * * * *